United States Patent

Joensen et al.

(10) Patent No.: US 7,820,867 B2
(45) Date of Patent: Oct. 26, 2010

(54) PROCESS FOR CONVERTING DIFFICULTY CONVERTIBLE OXYGENATES TO GASOLINE

(75) Inventors: Finn Joensen, Hørsholm (DK); Bodil Voss, Virum (DK); Jesper Nerlov, Værløse (DK)

(73) Assignee: Haldor Topsøe A/S, Lyngby (DK)

( * ) Notice: Subject to any disclaimer, the term of this patent is extended or adjusted under 35 U.S.C. 154(b) by 445 days.

(21) Appl. No.: 12/063,021

(22) PCT Filed: Aug. 16, 2006

(86) PCT No.: PCT/EP2006/008076

§ 371 (c)(1),
(2), (4) Date: Feb. 5, 2008

(87) PCT Pub. No.: WO2007/020068

PCT Pub. Date: Feb. 22, 2007

(65) Prior Publication Data

US 2008/0228021 A1    Sep. 18, 2008

(30) Foreign Application Priority Data

Aug. 18, 2005 (DK) ............... 2005 01163

(51) Int. Cl.
*C07C 1/00* (2006.01)
*C07C 27/00* (2006.01)

(52) U.S. Cl. .......... 585/310; 639/640; 639/733; 518/700; 518/715

(58) Field of Classification Search .......... 585/310, 585/639, 640; 518/700, 715
See application file for complete search history.

(56) References Cited

U.S. PATENT DOCUMENTS

| | | |
|---|---|---|
| 3,894,102 A | 7/1975 | Chang et al. |
| 3,998,898 A | 12/1976 | Chang et al. |
| 4,481,305 A | 11/1984 | Jorn et al. |
| 4,520,216 A | 5/1985 | Skov et al. |
| 5,177,114 A | 1/1993 | Van Dijk et al. |
| 2004/0122267 A1 | 6/2004 | Sher et al. |

FOREIGN PATENT DOCUMENTS

EP    0 448 019    9/1991

*Primary Examiner*—In Suk Bullock
(74) *Attorney, Agent, or Firm*—Dickstein Shapiro LLP

(57) ABSTRACT

Process for converting oxygenate compounds to hydrocarbons comprising the steps: (a) introducing a feed stream of synthesis gas to a synthesis section for the production of easily convertible oxygenates, (b) passing the effluent stream from said synthesis section containing easily convertible oxygenates to a gasoline synthesis section, (c) passing the effluent of said gasoline synthesis section to a separator and withdrawing from said separator hydrocarbons boiling in the gasoline boiling range, (d) admixing a recycle stream from the separator containing unconverted synthesis gas volatile hydrocarbons with the feed stream of synthesis gas of step (a), (e) introducing a feed containing difficulty convertible oxygenates to the synthesis section of step (a).

9 Claims, 4 Drawing Sheets

US 7,820,867 B2

PROCESS FOR CONVERTING DIFFICULTY CONVERTIBLE OXYGENATES TO GASOLINE

FIELD OF THE INVENTION

This invention relates to a process for converting difficultly convertible oxygenates to gasoline.

In particular it refers to an improved method of converting primarily easily convertible oxygenates such as methanol or methanol and dimethyl ether (DME) in combination and difficultly convertible oxygenates such as certain aliphatic and aromatic oxygenates over a zeolite catalyst into hydrocarbon products, the hydrocarbon products being useful as main constituents of gasoline, commonly known as a motor fuel. More specifically the invention relates to a process for the reduction of the coke formation induced by difficultly convertible oxygenates components contained in substances such as bio-oil, thereby increasing the catalyst cycle time during gasoline synthesis.

The term gasoline as it is commonly used covers a product from the petroleum industry which contains as the main fraction hydrocarbons boiling in the gasoline range, further characterised by the octane numbers expressing the quality of the fuel when used in gasoline motors (internal combustion engines). Some additives may be added to the hydrocarbons to obtain certain further qualities for the gasoline product. It is well known that gasoline products with low octane numbers can be blended with gasoline products with high octane numbers for the purpose of yielding satisfactory overall octane numbers.

As used herein the term gasoline shall refer to the wide range of hydrocarbons boiling in the gasoline boiling range of 120° C. to 200° C. and holding proper gasoline qualities, either alone or in mixture with other sources of gasoline. The quality requirements are primarily met by hydrocarbons with a carbon number of 5 or more, for short $C_{5+}$.

BACKGROUND OF THE INVENTION

Gasoline may be produced from refining crude oil through several processes comprising distillation and cracking. The synthesis of gasoline may also be effected by catalytic conversion of easily convertable oxygenates such as methanol or methanol and dimethyl ether (methanol/dimethyl ether) over zeolites, e.g. ZSM-5, at temperatures between 300° C. and 600° C. and pressures from atmospheric to few hundred bars, preferably from atmospheric to 100 bar. Typical WHSV (weight hour space velocity) of $C_1$ oxygenate equivalents is in the range 0.2-10. The catalytic conversion of methanol to gasoline is described in more detail by Chang in "Methanol to Hydrocarbons", Catal. Rev. 25 (1983)1.

Although the conversion of methanol or methanol/dimethyl ether into gasoline is generally referred to as the Methanol-to-Gasoline (MTG) process, oxygen-containing hydrocarbons (oxygenates) other than methanol are easily converted in the MTG process. The group of easily convertible oxygenates is not confined to methanol and/or dimethyl ether (DME), but comprises apart from alcohols and ethers, esters, long chain aldehydes, ketones and their analogues as described in U.S. Pat. No. 3,998,898. Apart from the desired portion of especially $C_{5+}$ gasoline products and co-produced water gasoline synthesis results in some by-production of olefins, paraffins, methane and products from thermal cracking (hydrogen, CO, $CO_2$). Subsequent separation and/or distillation ensures the upgrading of the raw hydrocarbon product mixture to useful gasoline. Naturally, a high yield of the useful gasoline products is desirable for obtaining proper process economy.

In the synthesis of gasoline according to the MTG process the basic feed is methanol or other oxygenates which are evaporated and then introduced to the process. In a variant of the MTG process the basic feed is synthesis gas which in a first step is partly converted into methanol or methanol/dimethyl ether and, in a second step, the methanol or methanon/dimethyl ether is converted into gasoline and unconverted synthesis gas is recycled to the first step. In other words, the synhesis of methanol or methanol/dimethyl ether is integrated with the synthesis of gasoline. The integrated process is described in more detail by Topp-Jørgensen in Stud. Surf. Sci. Catal. 36 (1988) 293.

In this integrated process methanol is synthesized from synthesis gas, i.e. gas containing mainly $H_2$, CO and $CO_2$ according to the following reaction schemes:

$$CO_2 + 3H_2 \leftrightarrow CH_3OH + H_2O$$

$$CO + H_2O \leftrightarrow CO_2 + H_2$$

while the synthesis of DME is conducted by the dehydration of methanol according to the following scheme:

$$2CH_3OH \leftrightarrow DME + H_2O$$

Depending on the operating conditions more or less by-product is formed, primarily small amounts of higher alcohols, ketones, aldehydes and acids. Catalysts for the synthesis of methanol and dimethyl ether are well known in industrial practice. Typical examples of methanol synthesis catalysts are mixtures of Cu/Zn/Al oxides and, for dimethyl ether synthesis, acid catalysts, e.g. silica-alumina. The catalysts may be applied separately to convert synthesis gas to methanol and to convert methanol to dimethyl ether, respectively, or they may be combined to produce mixtures of methanol and dimethyl ether directly from synthesis gas. The combination may be effected by physically mixing the catalysts or they may be co-fabricated to combine all of the above catalytic functions in one and the same catalyst. It is characteristic to the class of Cu/Zn/Al-based methanol synthesis catalysts that they are also efficient hydrogenation catalysts.

The combined synthesis of methanol/dimethyl ether in the first step of the integrated process is normally preferred rather than synthesis of methanol only as the further conversion of methanol to DME in said first step reduces the heat evolved, and thereby the operating temperature in the second subsequent step, i.e. the gasoline synthesis section, which in turn ensures a higher yield of gasoline product and/or a cheaper gasoline synthesis.

It is known that, in the integrated gasoline synthesis process, synthesis gas containing hydrogen, carbon monoxide, carbon dioxide, proper in composition for the synthesis of methanol and/or DME, and inert components is mixed with a recycle stream from a separation step subsequent to the gasoline synthesis section. The recycle stream contains unconverted synthesis gas and volatile products from the gasoline synthesis. The admixture of synthesis gas and recycle stream is heated and passed to the methanol or methanol/DME synthesis section. The effluent from the methanol or methanol/DME synthesis section is normally mixed with a second recycle stream from the separator subsequent to the gasoline synthesis section to obtain a mixed feed containing easily convertible oxygenates, which is then passed to the gasoline synthesis section. The gasoline synthesis takes place in well known fixed bed and/or fluidised bed reactors. The effluent from the gasoline synthesis section and which is enriched in gasoline components and water, light olefinic hydrocarbons, methane and paraffins is cooled and passed to a separating unit where water, hydrocarbons and unconverted synthesis gas containing i.a. volatile hydrocarbons and hydrogen are separated, the latter stream normally being split in a purge stream, a first recycle stream and a second recycle stream. Thus, in the integrated gasoline synthesis process hydrogen, carbon monoxide and carbon dioxide are present in significant amounts in the methanol containing feed stream which enters the gasoline synthesis section. This process is normally referred to as TIGAS (Topsøe Integrated Gasoline Synthesis).

The conversion of easily convertible oxygenates such as methanol to gasoline as a stand-alone process is for instance known from U.S. Pat. No. 3,998,898. This citation teaches that difficultly convertible aliphatic oxygenates comprising the group of short chain aldehydes, carboxylic acids and anhydrides, glycols, glycerine and carbohydrates may be converted to gasoline products, though in a less satisfactory manner and with poorer catalyst cycle life as compared to the easily convertible oxygenates. Yet by co-feeding to the gasoline reactor easily convertible oxygenates with difficultly converted oxygenates at a temperature of at least 260° C. and a space velocity of 0.5 to 50 LHSV (Liquid Hour Space Velocity) a higher yield of gasoline is obtained than when either reactant type is used alone. However, by co-feeding to the gasoline reactor the difficultly convertible oxygenates a substantial fraction of the oxygenate carbon ends up as carbon oxides in the effluent from the gasoline reactor, i.e. the ratio of carbon in the hydrocarbon product with respect to the carbon in the feed to the gasoline reactor decreases. Part of the carbon loss as carbon oxides is related to the cracking of hydrocarbons, thus creating undesired attendant effects such as reduced catalyst cycle time in the gasoline reactor.

It is well known that the catalytic conversion of oxygenates into gasoline over acid catalysts like zeolites is accompanied by the formation of carbonaceous deposits, generally referred to as "coke" which is undesirable because it deactivates the catalyst, and because it represents a loss of carbon value. The coke formation rate depends inter alia on the zeolite applied, the feed components and on the operating conditions in particular temperature. The catalytic coke must be removed from the catalyst to regain catalytic activity, typically by burning off the coke under controlled conditions.

Apart from the coke formation associated with the catalytic conversion of oxygenates into gasoline also thermal cracking of less stable oxygenates (difficultly convertible) may lead to coke formation not only depositing on the catalyst surface but also on reactor internals, in heat exchangers, valves and other equipment.

Coke associated with the catalytic conversion, formed only on the interior and exterior surface of the catalyst, must be distinguished from the coke formed by thermal cracking of less stable oxygenates, e.g. by condensation/polymerisation of precursors which may take place when preheating and introducing the oxygenate feed to the conversion catalyst and which results in coke lay-down on the external surface of the catalyst particles (pellets, extrudates, etc.) and elsewhere on the surface of reactor internals, exchangers, valves, etc. The formation of coke due to thermal cracking is thus particularly undesirable because it causes plugging not only in the reactor but also in the feed system upstream the catalyst bed, i.e. in equipment which does not tolerate the excessive temperatures associated with removal of coke by controlled burn-off.

The catalyst cycle time as defined herein is the length of the period, wherein the catalyst exhibits proper catalytic activity before the catalyst must be regenerated by burning off the coke. Short catalyst cycle time means that an expensive type of reactor must be employed e.g. with continuous regeneration of catalyst circulated between reactor and regenerator or that several reactors in parallel must be employed with frequent shifts in operation mode (synthesis or regeneration) and being equipped with complex control. An increased catalyst cycle time benefits the process by a reduction in investment and improved process efficiency.

Apart from a process with increased catalyst cycle time it would also be desirable to be able to provide a process which is less sensitive (i.e. more robust) to changes in co-feed composition, so that the co-feed to the integrated gasoline process is able to treat a wide range of difficultly convertible oxygenates, including particularly difficultly convertible aromatic compounds and short-chained aldehydes, such as phenol, 2-methoxy phenol (anisol) and acetaldehyde.

Examples of substances containing difficultly convertible oxygenates of interest for the co-feeding into a gasoline synthesis are e.g. bio-oil products prepared by high pressure liquefaction or by pyrolysis.

Bio-fuels have found interest due to their $CO_2$ neutrality to the environment, thus the $CO_2$ released during combustion corresponds to the amount consumed through the growth of the plant of origin, e.g. wood. Sources of bio-oils are forest and agricultural waste such as sawdust, bark, or sugar cane waste bagasse. Bio-oil products have been shown to contain highly oxygenated compounds (difficultly convertible compounds), the exact composition of which depends upon the type of raw material source and processing conditions. The bio-oil product is furthermore rather instable with respect to secondary reactions such as condensation and polymerisation making bio-oils of limited potential as fuels. In particular, the presence of difficultly convertible aromatic compounds and short-chained aldehydes, such as phenol, 2-methoxy phenol (anisol) and acetaldehyde, has prevented the otherwise appealing utilisation of bio-oil in gasoline synthesis.

For instance, in "Transformation of Oxygenate Components of Biomass Pyrolysis Oil on a HZSM-5 zeolite" I&II (Ind. Eng. Chem. Res., Vol. 43, No. 11, 2004) by Gayubo et al. the conversions of selected model components over HZSM-5 was investigated. It was found, in conclusion, that short chain aldehydes and aromatics, such as acetaldehyde and phenol and 2-methoxy phenol (anisol), all of which are common constituents in bio-oil, exhibited low reactivity towards gasoline production and caused severe coke formation. Hence, due to the problems associated with said oxygenates it is normally considered more advantageous that phenols and aldehydes, as materials of economic interest, be separated from the oxygenate mixture before being passed over a zeolite for gasoline production.

In "Catalytic co-processing of biomass-derived pyrolysis vapours and methanol" by Horne et al. (J. of Analytical and Applied Pyrolysis, 34 (1995) 87-108)) various ratios of methanol and bio-oil were used in the co-feed of a hydrocarbon process conducted over a zeolite (ZSM-5) catalyst. The amount of coke generated by the bio-oil, containing a complex mixture of oxygenates, showed to be more than 4 times the amount of coke generated by feeding 100% methanol at 500° C. The coke formation was found to be a linear function of the fraction of bio-oil (balanced by methanol).

Bio-oil is made up of two classes of compounds originating from the cellulose and lignin parts of the pyrolysed biomass. The lignin break-down components are phenol derivatives, while the cellulose degradation part consists of mainly aldehydes, hydroxyaldehydes and alcohols and acids, typical components being furfural, furfuryl alcohol and short chain aldehydes such as acetaldehyde, hydroxyacetaldehyde, glyoxal, glycolic acid and acetol. The unsaturated nature of the product mixture may explain its relatively poor thermal stability, i.e. the bio-oil polymerizes and causes clogging upon heating. If the bio-oil is to be converted to a desirable gasoline fuel product in a manner where the fuel value of the bio-oil is largely maintained and where its instability is overcome the usefulness and thereby the value of bio-oil will be increased.

It is known that in the conversion of methanol and methanol/dimethyl ether over ZSM-5 and similar zeolites, durene (1,2,4,5-tetramethylbenzene) forms in relatively high amounts in the gasoline synthesis from methanol/dimethylether over HZSM-5. If present in the gasoline in excessive amounts (above 4-7 percent weight) durene may cause clogging of the fuel system in cold weather, in particular it may cause problems in the engine carburator system. Thus, excessive durene formation is undesirable in the gasoline synthesis. Durene may be removed from the gasoline product by subjecting a higher-boiling fraction, rich in durene, to a mild hydrocracking. This, however, incurs an additional cost of processing. It is generally believed that the formation of durene is favoured by increased pressure and therefore operation at the lowest possible pressure is normally required. It would be desirable that the level of durene in the gasoline product be kept at a low level as an increased removal of durene gives rise to both increased investment and loss of valuable gasoline product.

SUMMARY OF THE INVENTION

It is therefore an object of the invention to provide a process for gasoline production with less propensity for coke formation and thereby longer catalyst cycle time in the gasoline synthesis.

It is a further object of the invention to provide a process for the production of gasoline which is less sensitive to the use of a wide range of difficultly convertible oxygenates, including bio-oils.

It is yet another object of the invention to provide a process for the production of gasoline with reduced durene content in the gasoline product.

These and other objects are achieved by the process of the invention.

Accordingly, in the invention we provide a process for converting oxygenate compounds to hydrocarbons comprising the steps:

(a) introducing a feed stream of synthesis gas to a synthesis section for the production of easily convertible oxygenates,
(b) passing an effluent stream from said synthesis section containing easily convertible oxygenates to a gasoline synthesis section,
(c) passing the effluent of said gasoline synthesis section to a separator and withdrawing from said separator hydrocarbons boiling in the gasoline boiling range,
(d) admixing a recycle stream from the separator containing unconverted synthesis gas and volatile hydrocarbons with the feed stream of synthesis gas of step (a),
(e) introducing a feed containing difficultly convertible oxygenates to the synthesis section of step (a).

We have found that substances containing difficultly convertible oxygenates may synergistically be converted to a desired gasoline product without prior separation of e.g. short chain aldehydes and phenolic aromatics, by adding said difficultly convertible substances to the synthesis section for the production of easily convertible oxygenates in an integrated process comprising a gasoline synthesis loop, rather than adding the difficultly convertible sub-stances directly to the gasoline synthesis section.

By the integrated process it is possible to conduct the synthesis of easily convertible oxygenates and the gasoline synthesis at substantially the same pressure level.

Preferably the stream product of easily convertible oxygenates contains methanol or methanol/DME.

The substances containing difficultly convertible oxygenates are preferably co-fed to the integrated gasoline synthesis in a weight ratio of 0.05:1 relative to the methanol/dimethyl ether formed, more preferably in a weight ratio of 0.1:1, for example 0.1:0.8, often 0.1:0.5.

It is believed that the hydrogen present in the gasoline reactor is potentially capable of hydrogenating certain intermediate products and thereby plays an active role through the reaction path influencing the gasoline product distribution as finally obtained.

The feed of difficultly convertible oxygenates may be added as a separate stream to the synthesis section for the production of easily convertible oxygenates or may be introduced as admixture to the feed stream of synthesis gas.

In a preferred embodiment of the invention, the synthesis section for the production of easily convertible oxygenates consists of a one step methanol synthesis, or two step methanol synthesis, or a two step methanol synthesis followed by a DME synthesis, or a methanol synthesis step followed by a combined methanol and DME synthesis step and a DME synthesis step or a one step combined methanol and DME synthesis. It would be understood that the number of possible combinations of means of co-feeding into the methanol/DME synthesis loop and the layouts of the methanol or methanol/dimethyl ether synthesis is large. Any combinations deductible is therefore to be regarded as embodiments of present invention. The formation of DME as an additional easily convertible oxygenate enables that the conversion of synthesis gas into methanol and DME can be carried out at lower operating pressures, thus reducing the need for the eventual compression of synthesis gas.

By the invention, the loss of oxygenates through by-product formation in the gasoline synthesis as carbon oxides is counteracted by employing a gasoline synthesis which is integrated with the oxygenate synthesis by taking advantage that the carbon oxides formed in the gasoline synthesis are reactants in the synthesis of methanol. Thus, the pre-sent invention provides an additional advantage by recycling and re-using such byproduct carbon oxides to the oxygenate synthesis section.

The resulting reduction in the thermal and to some extent catalytic coke formation over the catalyst contained in the gasoline reactor may be explained by the complex hydrogenation and methylation reactions taking place in the methanol or methanol/dimethyl ether reactor(s) upstream of the gasoline reactor.

In another embodiment the inventive process comprises also admixing a recycle stream from the separator containing unconverted synthesis gas and volatile hydrocarbons with the effluent stream of step (b); that is, the recycle stream is added to the stream containing easily convertible oxygenates, such as methanol and/or DME prior to entering the gasoline synthesis section. This enables a high partial pressure of hydrogen in the gasoline synthesis reactor, thereby further reducing the coking tendency of the gasoline catalyst and further increasing the catalyst cycle time. A high hydrogen pressure in the gasoline reactor enables also the production of a more stable gasoline product, as the content of olefins in the gasoline is significantly reduced.

Normally, if conversion to gasoline takes place in an adiabatic reactor, e.g. a fixed bed, substantial temperature rises over the catalyst bed may occur. The yield of gasoline product, i.e. the fraction of useful $C_{5+}$ components obtained from the conversion of oxygenates is influenced by the operating temperature: an increase in operating temperature decreases the gasoline yield and increases the rate of coke formation, thus reducing the catalyst cycle time. In the invention the co-feeding of the substance(s) containing difficultly convertible oxygenate increases the specific heat capacity of the feed to the gasoline reactor, an consequently a lower adiabatic temperature rise is achieved.

Substances containing difficultly convertible oxygenates as used herein are defined by its dry composition comprising hydroxyacetaldehyde, acetol, glyoxal and glycolic acid/-esters up to 80 wt %, acetic acid and esters thereof up to 30 wt %, furfural, furfuryl alcohol and derivatives thereof up to 50%, and phenol and phenol derivatives such as cresols, anisol, catechol, guajacol, eugenol in the range 1-100%. Further components contained in the substance may comprise easily convertible oxygenates.

The difficultly convertible oxygenates may be differentiated from the easily convertible oxygenates by the so-called R-values as described in U.S. Pat. No. 3,998,898. A given oxygenate is given the empirical formula:

$$C_nH_{m-2p}pH_2O$$

where
n is the number of carbon atoms in the molecule,
p is the number of oxygen atoms, and
m is the number of hydrogen atoms.

The R-value is defined by:

$$R=(m-2p)/n$$

According to this definition difficultly convertible oxygenates are defined as those having R-values equal or less than 1 including carboxylic acids irrespective of their R-value, whereas easily convertible oxygenates are non-carboxilic acids having R-values greater than 1. For instance, methanol ($CH_3OH$) and DME (($CH_3$)2O), which are known as easily convertible oxygenates, have both R values of 2. On the other hand, the difficultly convertible acetaldehyde ($CH_3CHO$), phenol ($C_6H_5OH$) and anisol ($C_6H_5OCH_3$) have R values of 1.0, 0.67 and 0.86, respectively.

As described in the above-mentioned U.S. Pat. No. 3,998, 898, the R value in a substance is cumulative. Thus, a substance used as co-feed in the invention may consist of a mixture of easily and difficultly convertible compounds. The total cumulative value of R must be equal or less than 1 if the substance (co-feed) is to be classified as difficultly convertible.

The following table resumes the R-values of a number of compounds:

| Compound | Formula | Net Formula | R |
| --- | --- | --- | --- |
| Formaldehyde | $CH_2O$ | $OH_2$ | 0 |
| Methanol | $CH_3OH$ | $CH_4$ | 2 |
| Acetaldehyde | $CH_3CHO$ | $C_2H_4O$ | 1 |
| Hydroxyaldehyde | $CH_2OHCHO$ | $C_2H_4O_2$ | 0 |
| Glyoxal | $(CHO)_2$ | $C_2H_2O_2$ | −1 |
| Acetol | $CH_2OHC(O)CH_3$ | $C_3H_6O_2$ | 0.67 |
| Ethanol | $C_2H_5OH$ | $C_2H_6O$ | 2 |
| Dimethyl Ether | $(CH_3)_2O$ | $C_2H_6O$ | 2 |
| Acetone | $CH_3C(O)CH_3$ | $C_3H_6O$ | 1.33 |
| Acetic acid | $CH_3COOH$ | $C_2H_4O_2$ | 0 |
| Propanol | $C_3H_6OH$ | $C_3H_8O$ | 2 |
| Methyl acetate | $CH_3COOCH_3$ | $C_3H_6O_2$ | 0.67 |
| Ethyl acetate | $CH_3COOC_2H_5$ | $C_4H_8O_2$ | 1 |

-continued

| Compound | Formula | Net Formula | R |
| --- | --- | --- | --- |
| Diethyl ether | $(C_2H_5)_2O$ | $C_4H_{10}O$ | 2 |
| i-Butanol | $C_4H_9OH$ | $C_4H_{10}O$ | 2 |
| Propionaldehyde | $C_2H_5CHO$ | $C_3H_6O$ | 1.33 |
| Furfural | $C_4H_4O(CHO)$ | $C_5H_4O_2$ | 0 |
| Furfuryl alcohol | $C_4H_4OCH_2OH$ | $C_5H_6O_2$ | 0.4 |
| Phenol | $C_6H_5OH$ | $C_6H_6O$ | 0.67 |
| Anisol | $C_6H_5OH$ | $C_6H_8O$ | 0.86 |
| Catechol | $C_6H_4(OH)_2$ | $C_6H_6O_2$ | 0.33 |
| Guajacol | $C_6H_4(OH)(OCH_3)$ | $C_6H_8O_2$ | 0.57 |
| Cresol | $C_6H_4(CH_3)(OH)$ | $C_6H_8O$ | 0.86 |
| Cresolol | $C_6H_3(CH_3)(OH)(OCH_3)$ | $C_8H_{10}O_2$ | 0.75 |
| Eugenol | $C_6H_3(C_3H_5)(OH)(OCH_3)$ | $C_{10}H_{12}O_2$ | 0.8 |
| Naphthol | $C_{10}H_7OH$ | $C_{10}H_8O$ | 0.6 |

Accordingly, the feed containing difficultly convertible oxygenates includes compounds selected from the group consisting of formaldehyde, acetaldehyde, hydroxyaldehyde, glyoxal, acetol, acetic acid, MeOAc, EtOAc, furfural, furfuryl alcohol, phenol, anisol, catechol, guajacol, cresol, cresolol, eugenol, naphtol or mixtures thereof.

For example, the feed containing difficultly convertible oxygenates may advantageously be a bio-oil, which may or may not be mixed with easily convertible oxygenates such as methanol.

By the invention it is also possible to only introduce particularly difficultly convertible oxygenates like acetaldehyde and aromatic compounds, specifically phenol and 2-methoxy phenol (anisol), into the synthesis section for the production of easily convertible oxygenates, while other difficultly convertible oxygenates, excluding for example said aromatic compounds, are introduced to the gasoline synthesis section. Accordingly, in yet another embodiment of the invention the feed of difficultly convertible oxygenates comprises as major components acetaldehyde, the aromatic compounds phenol and 2-methoxy phenol (anisol) or a mixture thereof. Other difficultly convertible oxygenates may then be added directly to the gasoline synthesis section.

By major components is meant that at least 50% wt., preferably at least 70% wt., normally at least 80% wt. of the feed containing difficultly convertible oxygenates is made of acetaldehyde, the aromatic compounds phenol and 2-methoxy phenol (anisol) or a mixture thereof.

The zeolite catalyst used for the conversion of oxygenates to gasoline products may be any zeolite type being known as useful for the conversion of oxygenates to gasoline range boiling hydrocarbons. Preferred types are those with a silica to alumina mole ratio of at least 12 and pore sizes formed by up to 12 membered rings, preferably 10 membered. Examples of such zeolites are ZSM-5, ZSM-11, ZSM-12, ZSM-23, ZSM-35 and ZSM-38. The manufacture of these is well known in the art and the catalysts are commercially available. Particularly preferred is the ZSM-5 in its hydrogen form, i.e. HZSM-5.

To enable a further decrease in the tendency to thermal coke formation, the co-feed of the substance containing difficultly convertible oxygenates is carefully preheated before being exposed to the main feed. Hence, in yet another embodiment of the invention the process further comprises subjecting the feed containing difficultly convertible oxygenates to instant vaporisation prior to contacting with the catalyst for the production of easily convertible oxygenates, e.g. by spraying the substance(s) as a liquid into a hot gas stream up front of the methanol or methanol/DME synthesis step. By this embodiment thermal coke formation is further prevented by short space time during heating and mixing with the diluting gas (main feed of gas entering the synthesis section for production of easily convertible oxygenates). Other advantageous methods of adding the feed containing difficultly convertible oxygenates is the combined preheating and heat exchanging, for instance by subjecting the feed containing difficultly convertible oxygenates to combined preheating by heat exchanging with the main feed stream, optionally in contact with the methanol or methanol/DME synthesis catalyst. This enables a gentle heating of the co-feed up to the required temperatures, normally about 220° C. Yet another method for gently introducing the co-feed comprises saturating a main or split synthesis gas stream from the methanol or methanol/dimethyl ether synthesis section with the feed containing difficultly convertible oxygenates. The saturation is conveniently carried out in a saturation tower, optionally charged with a catalyst active in hydrogenation, e.g. a methanol or methanol/dimethyl ether synthesis catalyst.

The invention is not limited to processes in which the production of easily convertible oxygenates is integrated with gasoline production. In the invention it is possible that the easily convertible oxygenates are produced in an independent (separate) process, wherein difficultly convertible oxygenates are co-fed. The resulting product containing easily convertible oxygenates may then be used for any other suitable application particularly gasoline production. By independent or separate process is meant a process that is not integrated with the gasoline synthesis section.

Accordingly, in the invention we also provide a process for the preparation of hydrocarbons by:
(a) introducing a feed stream of synthesis gas to a synthesis section for the production of easily convertible oxygenates,
(b) passing the effluent stream from said synthesis section containing easily convertible oxygenates to a separator and withdrawing from said separator a product stream enriched in easily convertible oxygenates,
(c) admixing a recycle stream from the separator containing unconverted synthesis gas with the feed stream of synthesis gas of step (a),
(d) introducing a feed containing difficultly convertible oxygenates to the synthesis section of step (a),
(e) converting said product stream enriched in easily convertible oxygenates to hydrocarbons.

This enables that the stream from the separator enriched in easily convertible oxygenates, preferably methanol or a mixture of methanol and DME, be passed to a storage tank for accumulation and further utilisation of said easily convertible oxygenates. The stored product of easily convertible oxygenates may then be transported to a separate plant for the production of gasoline, which may or may not be located nearby. Hence, the process may further comprise the step of converting said product stream enriched in easily convertible oxygenates to hydrocarbons boiling in the gasoline boiling range.

Thus, the process for converting said product stream enriched in easily convertible oxygenates to hydrocarbons (step (e)) comprises the steps:
(f) passing a stream of easily convertible oxygenates to a gasoline synthesis section,
(g) passing the effluent of said gasoline synthesis section to a separator and retrieving from said separator hydrocarbons boiling in the gasoline boiling range,
(h) admixing a recycle stream from the separator containing volatile hydrocarbons with the stream of easily convertible oxygenates of step (f).

BRIEF DESCRIPTION OF THE DRAWINGS

The invention is further illustrated by the accompanying drawings in which.

DETAILED DESCRIPTION OF THE PREFERRED EMBODIMENT

Figure 1:
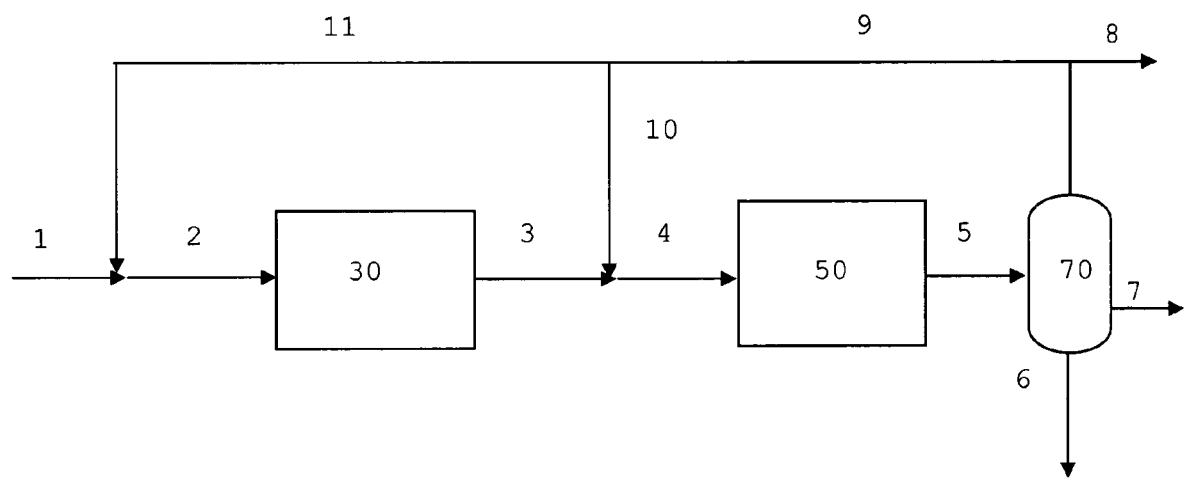
FIG. 1 shows a scheme of an integrated methanol or methanol/DME and gasoline synthesis loop according to the prior art.

In FIG. 1 common unit operations such as heating, cooling and compression steps are left out for simplicity. Synthesis gas 1 containing hydrogen, carbon monoxide, carbon dioxide, proper in composition for the synthesis of methanol and/or dimethyl ether and inert components is mixed with a recycle stream 11 containing unconverted synthesis gas and volatile hydrocarbons. The admixture 2 is heated to about 220° C. and passed to the methanol or methanol/dimethyl ether synthesis section 30. The syntheses of methanol or methanol/dimethyl ether are catalysed by well known commercially available catalysts. The effluent 3 from the methanol or methanol/dimethyl ether synthesis 30 is optionally mixed with a second recycle stream 10 to obtain a mixed feed 4 containing oxygenate being passed at about 350° C. to the gasoline synthesis section 50. The effluent 5 enriched in gasoline components and water, light olefinic hydrocarbons, methane and paraffins is cooled and passed to a three phase separator 70, where water 6, hydrocarbons 7 and unconverted synthesis gas containing volatile hydrocarbons are separated, the latter stream being split in a purge stream 8, and a recycle stream 9. The recycle stream 9 is optionally further divided in a first recycle stream 11 and a second recycle stream 10. Thus, when an integrated synthesis is employed hydrogen, carbon monoxide and carbon dioxide are present in significant amounts in the main feed stream 4 comprising methanol or methanol/dimethyl ether entering the gasoline reactor 50.

Figure 2:
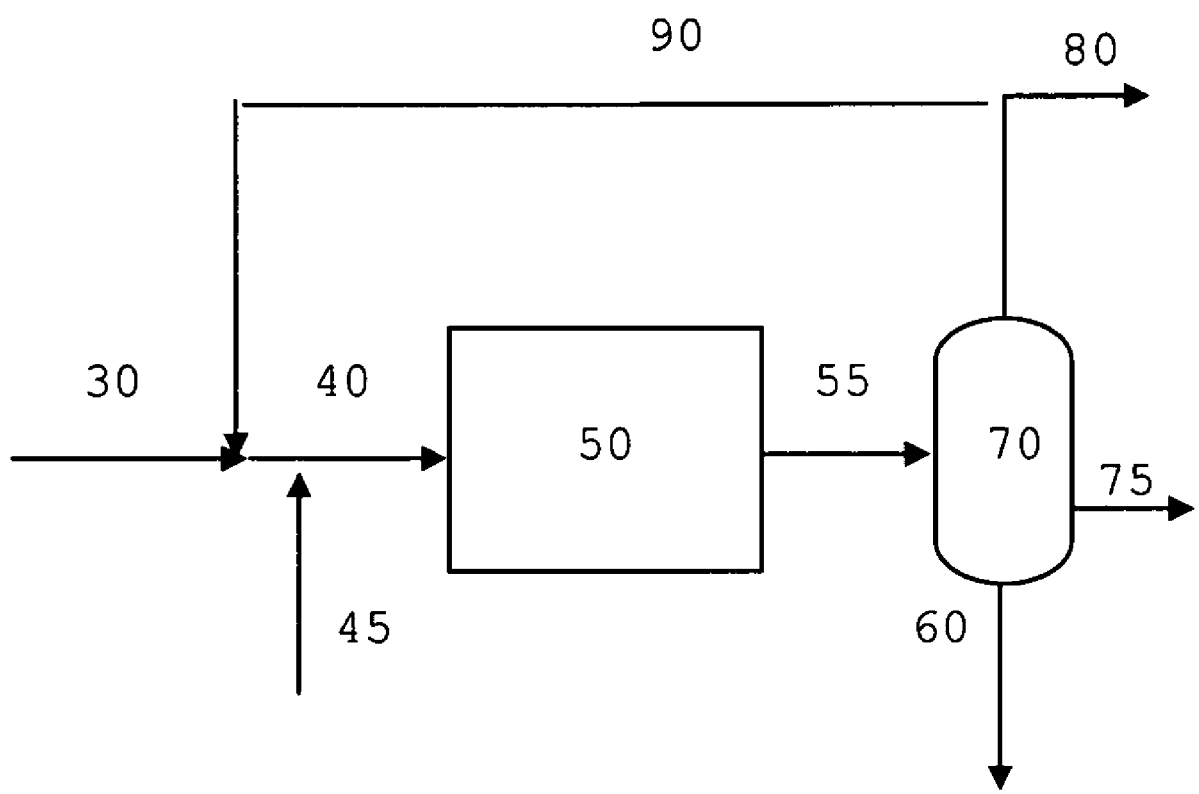
FIG. 2 shows a scheme of a gasoline synthesis loop as a stand-alone process according to the prior art with introduction of a co-feed of difficultly convertible oxygenates.

In FIG. 2 a gasoline synthesis section is shown. A stream of easily convertible oxygenates in the form of methanol or methanol/DME 30 is mixed with recycle stream 90 from three-phase separator 70 positioned downstream the gasoline reactor 50. Effluent 55 enriched in gasoline components and water, methane, light olefinic and paraffinic hydrocarbons, is cooled and passed to said separator, where water 60, hydrocarbons 75 and unconverted synthesis gas containing volatile hydrocarbons are separated, the latter stream being split in a purge stream 80 and recycle stream 90. A co-feed of difficultly convertible oxygenates 45 is admixed to the main feed of easily convertible oxygenates 30 or the admixture 40 prior to entering the gasoline synthesis section (gasoline reactor).

Figure 3:
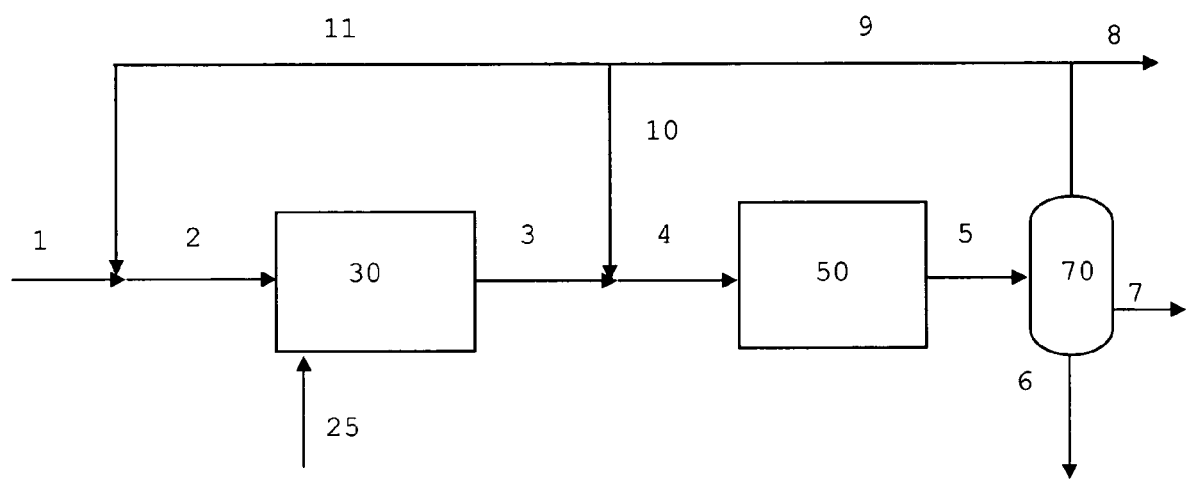
FIG. 3 shows a scheme of an integrated process according to one embodiment of the invention integrating the synthesis loop for production of methanol or methanol/DME and the gasoline synthesis loop together with a co-feed of difficultly convertible oxygenates.

FIG. 3 shows a preferred embodiment according to the invention, in which an integrated methanol or methanol/DME and gasoline synthesis loop as described in FIG. 1 is further provided with a co-feed stream 25 of difficultly convertible oxygenates which is introduced into the methanol/DME synthesis section 30.

Figure 4:
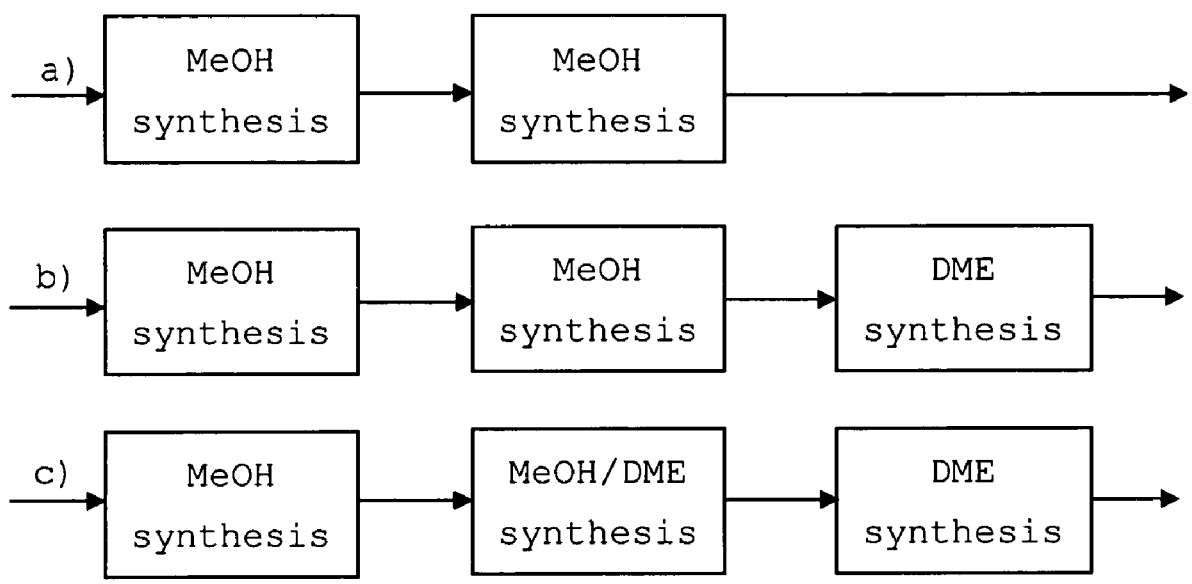
FIG. 4 shows examples of layouts for the methanol and the methanol/dimethyl ether synthesis.

The methanol or methanol/dimethyl ether synthesis section 30 may be laid out in numerous ways depending on the pressure level chosen and/or the capacity of the plant. In effect, the methanol synthesis may take place in one or more steps, the synthesis of dimethyl ether make take place in combination with the synthesis of methanol, either simultaneously or intermittently and/or in a final step. In FIG. 4 (a) exemplifies a two step methanol synthesis, (b) exemplifies a two step methanol synthesis followed by a DME synthesis and (c) exemplifies a methanol synthesis step followed by a combined methanol and DME synthesis step and a DME synthesis step.

The invention claimed is:

1. Process for converting oxygenate compounds to hydrocarbons comprising the steps
   (a) introducing a feed stream of synthesis gas to a synthesis section for the production of easily convertible oxygenates,
   (b) passing an effluent stream from said synthesis section containing easily convertible oxygenates to a gasoline synthesis section,
   (c) passing the effluent of said gasoline synthesis section to a separator and withdrawing from said separator hydrocarbons boiling in the gasoline boiling range,
   (d) admixing a recycle stream from the separator containing unconverted synthesis gas and volatile hydrocarbons with the feed stream of synthesis gas of step (a),
   (e) introducing a feed containing difficultly convertible oxygenates to the synthesis section of step (a)
   wherein the easily convertible oxygenates include compounds selected from the group consisting of methanol, ethanol, dimethyl ether, acetone, propanol, diethyl ether, ibutanol, propionaldehyde or mixtures thereof, and wherein the feed containing difficultly convertible oxygenates includes compounds selected from the group consisting of formaldehyde, acetaldehyde, hydroxyaldehyde, glyoxal, acetol, acetic acid, MeOAc, EtOAc, furfural, furfuryl alcohol, phenol, anisol, catechol, guajacol, creosol, cresolol, eugenol, naphtol or mixtures thereof.

2. Process according to claim 1, further comprising admixing a recycle stream from the separator containing unconverted synthesis gas and volatile hydrocarbons with the effluent stream of step (b).

3. Process according to claim 1, wherein the synthesis section for the production of easily convertible oxygenates consists of a one step methanol synthesis, or two step methanol synthesis, or a two step methanol synthesis followed by a DME synthesis, or a methanol synthesis step followed by a combined methanol and DME synthesis step and a DME synthesis step, or a one step combined methanol and DME synthesis.

4. Process according to claim 1, wherein the feed containing difficultly convertible oxygenates comprises as major components acetaldehyde, the aromatic compounds phenol and 2-methoxy phenol (anisol) or a mixture thereof.

5. Process according to claim 1, further comprising subjecting the feed containing difficultly convertible oxygenates to instant vaporization prior to contacting with the catalyst for the production of easily convertible oxygenates.

6. Process according to claim 1, further comprising subjecting the feed containing difficultly convertible oxygenates to combined preheating by heat exchanging with the main feed stream optionally in contact with the methanol or methanol/DME synthesis catalyst.

7. Process according to claim 1, further comprising saturating a main or split synthesis gas stream from the methanol or methanol/dimethyl ether synthesis section with the feed containing difficultly convertible oxygenates.

8. Process for the preparation of hydrocarbons by:
   (a) introducing a feed stream of synthesis gas to a synthesis section for the production of easily convertible oxygenates,
   (b) passing the effluent stream from said synthesis section containing easily convertible oxygenates to a separator and withdrawing from said separator a product stream enriched in easily convertible oxygenates,
   (c) admixing a recycle stream from the separator containing unconverted synthesis gas with the feed stream of synthesis gas of step (a),
   (d) introducing a feed containing difficultly convertible oxygenates to the synthesis section of step (a),
   (e) converting said product stream enriched in easily convertible oxygenates to hydrocarbons
   wherein the easily convertible oxygenates include compounds selected from the group consisting of methanol, ethanol, dimethyl ether, acetone, propanol, diethyl ether, i-butanol, propionaldehyde or mixtures thereof, and wherein the feed containing difficultly convertible oxygenates includes compounds selected from the group consisting of formaldehyde, acetaldehyde, hydroxyaldehyde, glyoxal, acetol, acetic acid, MeOAc, EtOAc, furfural, furfuryl alcohol, phenol, anisol, catechol, guajacol, creosol, cresolol, eugenol, naphtol or mixtures thereof.

9. Process according to claim 8 wherein step (e) comprises:
   (f) passing a stream of easily convertible oxygenates to a gasoline synthesis section,
   (g) passing the effluent of said gasoline synthesis section to a separator and retrieving from said separator hydrocarbons boiling in the gasoline boiling range,
   (h) admixing a recycle stream from the separator containing volatile hydrocarbons with the stream of easily convertible oxygenates of step (f).

* * * * *